(12) United States Patent
Terry

(10) Patent No.: US 7,820,284 B2
(45) Date of Patent: Oct. 26, 2010

(54) MICROBE-RESISTANT MEDICAL DEVICE, MICROBE-RESISTANT POLYMERIC COATING AND METHODS FOR PRODUCING SAME

(75) Inventor: Richard N. Terry, Conyers, GA (US)

(73) Assignee: C.R. Bard Inc., Murray Hill, NJ (US)

( * ) Notice: Subject to any disclaimer, the term of this patent is extended or adjusted under 35 U.S.C. 154(b) by 0 days.

(21) Appl. No.: 10/497,043

(22) PCT Filed: Dec. 3, 2002

(86) PCT No.: PCT/US02/38404

§ 371 (c)(1),
(2), (4) Date: Oct. 21, 2004

(87) PCT Pub. No.: WO03/047636

PCT Pub. Date: Jun. 12, 2003

(65) Prior Publication Data

US 2005/0064176 A1    Mar. 24, 2005

Related U.S. Application Data

(60) Provisional application No. 60/336,755, filed on Dec. 3, 2001.

(51) Int. Cl.
| B32B 5/16 | (2006.01) |
| B32B 27/36 | (2006.01) |
| B32B 27/06 | (2006.01) |
| B32B 27/40 | (2006.01) |
| B32B 15/04 | (2006.01) |
| B05D 1/40 | (2006.01) |
| B05D 3/02 | (2006.01) |
| B05D 1/36 | (2006.01) |
| B05D 5/00 | (2006.01) |

(52) U.S. Cl. .................. 428/323; 428/412; 428/423.1; 428/447; 428/457; 428/473.5; 428/474.4; 428/480; 428/500; 427/331; 427/372.2; 427/402; 427/407.1; 427/419.1; 427/421.1; 427/430.1

(58) Field of Classification Search ........................ None
See application file for complete search history.

(56) References Cited

U.S. PATENT DOCUMENTS

| 861,231 A | 7/1907 | Clark |
| 1,557,234 A | 10/1925 | Bechhold |
| 1,557,235 A | 10/1925 | Bechhold |
| 1,642,089 A | 9/1927 | Schreier |
| 1,685,204 A | 9/1928 | Schreier |
| 1,691,755 A | 11/1928 | Buttner |
| 2,283,883 A | 5/1942 | Conconi |
| 2,363,354 A | 11/1944 | Peacock |
| 2,421,079 A | 5/1947 | Narcus |
| 2,459,896 A | 1/1949 | Schwarz |
| 2,459,897 A | 1/1949 | Schwarz |
| 2,562,488 A | 7/1951 | Fuchs |
| 2,602,757 A | 7/1952 | Kantrowitz et al. |
| 2,639,997 A | 5/1953 | Drake et al. |
| 2,653,893 A | 9/1953 | Romans |
| 2,689,191 A | 9/1954 | Pessel |
| 2,689,809 A | 9/1954 | Fessler |
| 2,702,253 A | 2/1955 | Bergström |
| 2,758,106 A | 8/1956 | Bredereck et al. |
| 2,813,056 A | 11/1957 | Davis et al. |
| 2,813,059 A | 11/1957 | Davis et al. |
| 2,822,289 A | 2/1958 | Millard |
| 2,879,175 A | 3/1959 | Umblia et al. |
| 2,947,282 A | 8/1960 | Brown |
| 3,092,552 A | 6/1963 | Romans |
| 3,184,376 A | 5/1965 | Degoli |
| 3,228,881 A | 1/1966 | Thomas |
| 3,300,336 A | 1/1967 | Gagliardi et al. |
| 3,380,848 A | 4/1968 | Horowitz |
| 3,396,727 A | 8/1968 | Mount |
| 3,404,028 A | 10/1968 | Trask et al. |
| 3,561,995 A | 2/1971 | Wu et al. |
| 3,566,874 A | 3/1971 | Shepherd |
| 3,591,329 A | 7/1971 | Chromeček et al. |
| 3,598,127 A | 8/1971 | Wepsic |
| 3,610,247 A | 10/1971 | Jackson |
| 3,639,575 A | 2/1972 | Schmolka |
| 3,695,921 A | 10/1972 | Shepherd et al. |
| 3,699,956 A | 10/1972 | Kitrilakis et al. |
| 3,734,897 A | 5/1973 | Stoy |
| 3,761,590 A | 9/1973 | Fox |
| 3,822,238 A | 7/1974 | Blair et al. |

(Continued)

FOREIGN PATENT DOCUMENTS

AU          558588          2/1987

(Continued)

OTHER PUBLICATIONS

European Search Report, Jan. 25, 2007.

(Continued)

*Primary Examiner*—Sheeba Ahmed
(74) *Attorney, Agent, or Firm*—Greenblum & Bernstein, P.L.C.

(57) ABSTRACT

Microbe-resistant medical devices and methods of making these medical devices are provided. A base coat is applied to at least a portion of a surface of the device. That base coat includes one or more types of antimicrobial particles that are held in the base coat. A polymeric over coat is applied over at least a portion of the base coat. The over coat may be an organic soluble polymer, a water soluble polymer, a hydrogel or any other polymer capable of being coated onto a medical device. The polymer of the over coat is dissolvable in a solvent that does not dissolve the polymeric base coat during application of the over coat. The over coat remains free of the antimicrobial particles by not dissolving the base coat during the over coating process.

38 Claims, No Drawings

U.S. PATENT DOCUMENTS

| | | |
|---|---|---|
| 3,902,500 A | 9/1975 | Dryden |
| 3,953,545 A | 4/1976 | Stoy |
| 3,975,350 A | 8/1976 | Hudgin et al. |
| 4,054,139 A | 10/1977 | Crossley |
| 4,076,622 A | 2/1978 | Costin |
| 4,145,370 A | 3/1979 | Sreeves et al. |
| 4,156,066 A | 5/1979 | Gould et al. |
| 4,156,067 A | 5/1979 | Gould et al. |
| 4,197,220 A | 4/1980 | Rembaum et al. |
| 4,228,056 A | 10/1980 | Stoy |
| 4,252,677 A | 2/1981 | Smith |
| 4,252,678 A | 2/1981 | Smith |
| 4,255,550 A | 3/1981 | Gould et al. |
| 4,256,067 A | 3/1981 | Fukui et al. |
| 4,284,444 A | 8/1981 | Bernstein et al. |
| 4,327,721 A | 5/1982 | Goldin et al. |
| 4,339,337 A | 7/1982 | Tricot et al. |
| 4,358,388 A | 11/1982 | Daniel et al. |
| 4,359,558 A | 11/1982 | Gould et al. |
| 4,378,796 A | 4/1983 | Milhaud |
| 4,421,660 A | 12/1983 | Solc Nee Hajna |
| 4,436,855 A | 3/1984 | Higgins et al. |
| 4,443,577 A | 4/1984 | Higgins et al. |
| 4,476,590 A | 10/1984 | Scales et al. |
| 4,479,795 A | 10/1984 | Mustacich et al. |
| 4,483,688 A | 11/1984 | Akiyama |
| 4,539,234 A | 9/1985 | Sakamoto et al. |
| 4,540,631 A | 9/1985 | Boultinghouse |
| 4,542,169 A | 9/1985 | Costerton |
| 4,563,184 A | 1/1986 | Korol |
| 4,563,485 A | 1/1986 | Fox et al. |
| 4,564,361 A | 1/1986 | Akiyama |
| 4,569,673 A | 2/1986 | Tesi |
| 4,579,731 A | 4/1986 | Fox et al. |
| 4,581,028 A | 4/1986 | Fox et al. |
| 4,592,920 A | 6/1986 | Murtfeldt |
| 4,603,152 A | 7/1986 | Laurin et al. |
| 4,612,337 A | 9/1986 | Fox et al. |
| 4,615,705 A | 10/1986 | Scales et al. |
| 4,632,108 A | 12/1986 | Geil |
| 4,642,104 A | 2/1987 | Sakamoto et al. |
| 4,642,267 A | 2/1987 | Creasy et al. |
| 4,677,143 A | 6/1987 | Laurin et al. |
| 4,725,314 A | 2/1988 | Gulla et al. |
| 4,728,323 A | 3/1988 | Matson |
| 4,729,914 A | 3/1988 | Kliment et al. |
| 4,734,097 A | 3/1988 | Tanabe et al. |
| 4,738,782 A | 4/1988 | Yamauchi et al. |
| 4,775,585 A | 10/1988 | Hagiwara et al. |
| 4,789,720 A | 12/1988 | Teffenhart et al. |
| 4,810,543 A | 3/1989 | Gould et al. |
| 4,810,582 A | 3/1989 | Gould et al. |
| 4,820,292 A | 4/1989 | Korol et al. |
| 4,847,049 A | 7/1989 | Yamamoto |
| 4,849,223 A | 7/1989 | Pratt et al. |
| 4,871,790 A | 10/1989 | Lamanna et al. |
| 4,902,503 A | 2/1990 | Umemura et al. |
| 4,906,466 A | 3/1990 | Edwards et al. |
| 4,915,694 A | 4/1990 | Yamamoto et al. |
| 4,923,450 A | 5/1990 | Maeda et al. |
| 4,933,178 A | 6/1990 | Capelli |
| 4,948,739 A | 8/1990 | Charmot |
| 4,950,256 A | 8/1990 | Luther et al. |
| 4,952,411 A | 8/1990 | Fox et al. |
| 4,959,268 A | 9/1990 | Hagiwara et al. |
| 4,973,320 A | 11/1990 | Brenner et al. |
| 4,981,886 A | 1/1991 | Nako et al. |
| 4,999,210 A | 3/1991 | Solomon et al. |
| 5,013,306 A | 5/1991 | Solomon et al. |
| 5,019,096 A * | 5/1991 | Fox et al. .................. 600/36 |
| 5,037,395 A | 8/1991 | Spencer |
| 5,049,140 A | 9/1991 | Brenner et al. |
| 5,061,254 A | 10/1991 | Karakelle et al. |
| 5,061,424 A | 10/1991 | Karimi et al. |
| 5,102,401 A | 4/1992 | Lambert et al. |
| 5,120,816 A | 6/1992 | Gould et al. |
| 5,146,916 A | 9/1992 | Catalani |
| 5,173,531 A | 12/1992 | Kissel |
| 5,180,585 A | 1/1993 | Jacobson et al. |
| 5,201,724 A | 4/1993 | Hukins et al. |
| 5,227,434 A | 7/1993 | Katz |
| 5,290,585 A | 3/1994 | Elton |
| 5,320,908 A | 6/1994 | Sodervall et al. |
| 5,322,520 A | 6/1994 | Milder |
| 5,322,887 A | 6/1994 | Howell et al. |
| 5,326,567 A | 7/1994 | Capelli |
| 5,334,588 A | 8/1994 | Fox et al. |
| 5,334,691 A | 8/1994 | Gould et al. |
| 5,344,712 A | 9/1994 | Basil et al. |
| 5,357,636 A | 10/1994 | Dresdner et al. |
| 5,395,651 A | 3/1995 | Sodervall et al. |
| 5,413,788 A | 5/1995 | Edwards et al. |
| 5,451,424 A | 9/1995 | Solomon et al. |
| 5,454,886 A | 10/1995 | Burrell et al. |
| 5,476,509 A | 12/1995 | Keogh et al. ................... 623/1 |
| 5,478,563 A | 12/1995 | Erami |
| 5,492,763 A | 2/1996 | Barry et al. |
| 5,500,253 A | 3/1996 | Sanduja et al. |
| 5,503,840 A | 4/1996 | Jacobson et al. |
| 5,516,480 A | 5/1996 | Krall et al. |
| 5,520,664 A | 5/1996 | Bricault et al. |
| 5,524,642 A | 6/1996 | Rosenblatt |
| 5,567,495 A | 10/1996 | Modak et al. |
| 5,573,783 A * | 11/1996 | Desieno et al. ............. 424/490 |
| 5,595,750 A | 1/1997 | Jacobson et al. |
| 5,607,683 A | 3/1997 | Capelli |
| 5,616,338 A | 4/1997 | Fox et al. |
| 5,662,913 A | 9/1997 | Capelli |
| 5,685,961 A | 11/1997 | Pourrezaei et al. |
| 5,695,857 A | 12/1997 | Burrell et al. |
| 5,708,023 A | 1/1998 | Modak et al. |
| 5,709,672 A | 1/1998 | Illner |
| 5,709,870 A | 1/1998 | Yoshimura et al. |
| 5,725,510 A | 3/1998 | Hartmann et al. |
| 5,728,781 A | 3/1998 | Usuki et al. |
| 5,736,591 A | 4/1998 | Dunn |
| 5,739,178 A | 4/1998 | Powell et al. |
| 5,744,151 A | 4/1998 | Capelli |
| 5,747,178 A | 5/1998 | Sodervall et al. |
| 5,762,638 A | 6/1998 | Shikani et al. |
| 5,772,640 A | 6/1998 | Modak et al. |
| 5,788,687 A | 8/1998 | Batich et al. |
| 5,798,115 A | 8/1998 | Santerre et al. .......... 424/78.08 |
| 5,817,325 A | 10/1998 | Sawan et al. |
| 5,827,524 A | 10/1998 | Hagiwara et al. |
| 5,833,665 A | 11/1998 | Bootman et al. |
| 5,837,275 A | 11/1998 | Burrell et al. |
| 5,848,995 A | 12/1998 | Walder |
| 5,849,311 A | 12/1998 | Sawan et al. |
| 5,945,032 A | 8/1999 | Breitenbach et al. |
| 5,958,440 A | 9/1999 | Burrell et al. |
| 5,965,204 A | 10/1999 | Sodervall et al. |
| 5,965,610 A | 10/1999 | Modak et al. |
| 5,965,636 A | 10/1999 | Lark |
| 5,976,562 A | 11/1999 | Krall et al. |
| 5,985,308 A | 11/1999 | Burrell et al. |
| 5,993,910 A | 11/1999 | Carre et al. |
| 5,998,504 A | 12/1999 | Groth et al. |
| 6,015,816 A | 1/2000 | Kostyniak et al. |
| 6,017,553 A | 1/2000 | Burrell et al. |
| 6,028,127 A | 2/2000 | Yanagase et al. |
| 6,037,386 A | 3/2000 | Modak et al. |
| 6,063,849 A | 5/2000 | Morris et al. |
| 6,083,208 A | 7/2000 | Modak et al. |

| | | | |
|---|---|---|---|
| 6,106,505 A | 8/2000 | Modak et al. | |
| 6,106,853 A | 8/2000 | Cox et al. | |
| 6,150,004 A | 11/2000 | Oikawa et al. | 428/304.4 |
| 6,224,579 B1 | 5/2001 | Modak et al. | |
| 6,224,983 B1 | 5/2001 | Sodervall et al. | |
| 6,288,076 B1 | 9/2001 | Kostyniak et al. | |
| 6,296,863 B1 | 10/2001 | Trogolo et al. | 424/400 |
| 6,329,488 B1 | 12/2001 | Terry et al. | |
| 6,355,858 B1 | 3/2002 | Gibbins | |
| 6,399,689 B1 | 6/2002 | Screlette | |
| 6,478,861 B1 | 11/2002 | Kwan et al. | |
| 6,579,539 B2 | 6/2003 | Lawson | |
| 6,596,401 B1 | 7/2003 | Terry et al. | |
| 6,605,751 B1 | 8/2003 | Gibblins et al. | |
| 6,669,981 B2 | 12/2003 | Parsons et al. | |
| 6,756,124 B2 | 6/2004 | Kanamori et al. | |
| 6,908,681 B2 | 6/2005 | Terry et al. | |
| 7,029,755 B2 | 4/2006 | Terry et al. | |
| 7,087,249 B2 | 8/2006 | Burrell et al. | |
| 7,179,849 B2 | 2/2007 | Terry | |
| 2001/0010016 A1 | 7/2001 | Modak et al. | |
| 2003/0007985 A1 | 1/2003 | Chevalier et al. | |

FOREIGN PATENT DOCUMENTS

| | | |
|---|---|---|
| CA | 2 278 706 | 7/1998 |
| CZ | 147057 | 3/1972 |
| DE | 0038730 | 10/1981 |
| DE | 3026258 | 1/1982 |
| DE | 3228849 | 2/1984 |
| DE | 3300203 | 7/1984 |
| DE | 0206024 | 12/1986 |
| DE | 3302567 | 7/1990 |
| DE | 89 15 538 | 12/1990 |
| DE | 3942112 | 6/1991 |
| DE | 4115390 | 4/1992 |
| DE | 4316920 | 11/1994 |
| DE | 10128625 | 3/2002 |
| EP | 0038730 | 10/1981 |
| EP | 0206024 | 12/1986 |
| EP | 0229862 | 7/1987 |
| EP | 0251783 | 1/1988 |
| EP | 0301717 | 2/1989 |
| EP | 0302186 | 2/1989 |
| EP | 0318258 | 5/1989 |
| EP | 0328421 | 8/1989 |
| EP | 0379269 | 7/1990 |
| EP | 0399096 | 11/1990 |
| EP | 0400349 | 12/1990 |
| EP | 0699081 | 3/1999 |
| FR | 2330025 | 5/1977 |
| FR | 2109932 | 5/1979 |
| GB | 777679 | 6/1957 |
| JP | 59-218157 | 12/1984 |
| JP | 3-38504 | 2/1991 |
| JP | 4272764 | 9/1992 |
| JP | 4272765 | 9/1992 |
| JP | 5-117585 | 5/1993 |
| WO | 84/01721 | 5/1984 |
| WO | 85/02190 | 5/1985 |
| WO | 86/02006 | 4/1986 |
| WO | WO-9211877 A1 | 7/1992 |
| WO | 92/18098 | 10/1992 |
| WO | 94/27652 | 12/1994 |
| WO | 97/31709 | 9/1997 |
| WO | WO-0030697 A1 | 6/2000 |
| WO | 01/53414 | 7/2001 |
| WO | WO-0153414 A1 | 7/2001 |
| WO | WO-0218003 A1 | 3/2002 |
| WO | 2007130734 | 11/2007 |

OTHER PUBLICATIONS

English Language Abstract of DE 3228849.
English Language Abstract of DE 3300203.
English Language Abstract of DE 3302567.
English Language Abstract of DE 3942112.
English Language Abstract of DE 4115390.
ICI Polyarethanes Books, by George Woods, published by John Wiley and Sons, New York, N.Y., 1987.
Baselski V S, et al. "The standardization of criteria for processing and interpreting laboratory specimens in patents with suspected ventilator-associated pneumonia." Chest 1992; 102[suppl]:571S-579S.
Baron, et al. "Classification and identification of bacteria." In: Murray P R, ed. Manual of Clinical microbiology. Washington, D.C.: ASM Press, 1995; 249-264.
Marquette, et al. "Characterization of an animal model of ventilator-acquired pneumonia." Chest 1999; 115: 200-209.
Abstract of "Reaction of the bacterial load by the silver-coated endotracheal tube (SCET), a laboratory investigation" Hartmann et al, Technology and Healthcare 1999, vol. 7(5), p. 359-370, Dialog Access No. 10188995-20008765.
Maki et al., "An Attachable Silver Impregnated Cuff for Prevention of Infection With Central Venous Catheters: A Prospective Randomized Multicenter Trial," American Journal of Medicine, 1988, vol. 85, pp. 307-314.
Chemical Abstract No. 118:45828x, Koide et al.
Chemical Abstract No. 118:45829y, Koide et al.
Chemical Abstract No. 79:105832g, Stoy et al.
Chemical Abstract No. 88:51681x, Sulc et al.
Wrobleski, D. A. et al., "Surface Modification of Poly(ether urethane) by Chemical Infusion and Graft Polymerization", Progress of Biomedical polymers, pp. 192-204, 1988. [Chemical Abstract No. 114:234998f, Wrobleski, et al.].
R. Laperuta, et al, "Preperation and Characterization of Silver Colloid/Polymer Composite Nonlinear optical materials," Department of Chemistry, SPIE1497 (19910*-May 10, Dallas, Texas).
Olsen, M.E., et al., "Silver-Coated Endotracheal Tubes Associated with Reduced Ventilator-Associated Pneumonia (VAP) in Dogs", Respiratory and Critical Care medicine, 2001, vol. 163, No. 5, p. A754.
Olsen, M.E., et al., "Silver-coated Endotracheal Tubes Associated with Reduced Bacterial Burden in the Lungs of Mechanically Ventilated Dogs", Laboratory and Animal Investigations, 2002, vol. 121, No. 3, pp. 863-870.
U.S. Appl. No. 11/967,795 to Richard N. Terry, filed Dec. 31, 2007 and entitled "Antimicrobial Compositions Containing Colloids of Oligodynamic Metals".
U.S. Appl. No. 11/967,805 to Richard N. Terry, filed Dec. 31, 2007 and entitled "Antimicrobial Compositions Containing Colloids of Oligodynamic Metals".
English language Abstract of DE10128625.
English language Abstract of JP 3-38504.
English language Abstract of JP 4272764.
English language Abstract of JP4272765.
English language Abstract of JP 5-117585.
Canadian Office Action dated Oct. 13, 2009.
Official Action issued in connection with patent family member EP 02804480.8, dated Dec. 3, 2009.
Fourth Supplemental Information Disclosure Statement filed Mar. 4, 2009.
EP Official Communication dated Oct. 29, 2007.
Canadian Office Action issued in connection with counterpart Canadian application No. 2,468,780 on Jul. 29, 2010.

* cited by examiner

MICROBE-RESISTANT MEDICAL DEVICE, MICROBE-RESISTANT POLYMERIC COATING AND METHODS FOR PRODUCING SAME

CROSS-REFERENCE TO RELATED APPLICATIONS

This application is related to and claims the benefit of the filing date of U.S. Provisional Application No. 60/336,755, filed Dec. 3, 2001, which is incorporated herein by reference.

FIELD OF THE INVENTION

The present invention relates to coated microbe resistant medical devices that are for internal or external use with humans or animals, and methods of making these medical devices.

BACKGROUND OF THE INVENTION

Medical devices used for patient treatment can be a source of microbial (bacterial or fungal) infection in such patients. For example, insertion or implantation of a catheter into a patient can introduce microbes and/or, when left in place for prolonged periods of time, permit the introduction of microbes during long-term exposure of the catheter exit site to the environment. In addition, long-term catheter use often produces a biofilm on the catheter surface, which facilitates the development of infection that can cause patient discomfort and compromise patient health.

Microbial infection may be prevented by bonding an antimicrobial agent to a medical device. For example, U.S. Pat. No. 5,476,509 describes a catheter having a polymeric coating that has an antibiotic agent covalently or ionically bound thereto. Similarly, U.S. Pat. No. 5,798,115 describes a catheter having a polymer coating that has an antibiotic covalently bound to the polymer backbone. Bacteria kept in contact with these catheters for prolonged periods of time may be killed. However, these catheters are not effective at killing bacteria introduced into the body during insertion of the catheter. Because the antibiotic is attached to the catheter, the bacteria are able to migrate away from the catheter to avoid the antibiotic effect.

An antimicrobial catheter that is coated with a matrix-forming polymer in which an antibiotic agent is incorporated in the polymer coating is described in U.S. Pat. No. 5,019,096. Because the antibiotic is not covalently bound to the polymer, it is able to diffuse away from the catheter to attack organisms in the surrounding area.

However, the incorporation of antimicrobial agents into medical device coatings via insoluble particles (i.e., particles that are not soluble in the solvents used to coat the medical device) has produced unsatisfactory results, especially when dip or spray coating techniques are used to coat medical devices. For example, the insoluble antimicrobial particles tend to settle out from the solution used during coating. When particles settle from the solution, the concentration of the antimicrobial particles in the resulting coating is reduced over time during manufacturing, thereby reducing the manufacturer's ability to control the antimicrobial agent concentration on the device.

In addition, the antimicrobial particles can agglomerate in the coating solution into larger particles (from sizes of less than 4 microns to sizes from 10 to 100 microns or more). This can produce particles that are large enough to be felt on the surface of a coated device, and, if large enough, these agglomerated particles can produce patient discomfort. For example, particles larger than about 50 microns can usually be felt by a patient upon insertion of a Foley catheter into the urethra.

Particles smaller than 50 microns can also create problems. Although smaller particles in the range of 10 to 50 microns are not readily felt by patients, microscopic examination reveals that these particles produce coating surfaces that are bumpy or micro-rough. A micro-rough surface has a higher surface area than a smooth coated surface and this tends to increase the attachment of bacteria and other microorganisms. The increased surface area for microbial attachment and increased tissue irritation due to a rough catheter surface significantly reduces the ability of the antimicrobial coating to fight infection. Thus, there is a need for negating the potentially adverse effects that insoluble antimicrobial particle agglomeration can have on the performance of a coated medical device.

The problems associated with insoluble antimicrobial particles are especially relevant to antimicrobial coatings applied to catheters and, in particular, to Foley catheters.

SUMMARY OF THE INVENTION

To counteract the problems associated with incorporation of one or more types of antimicrobial particles into medical device coatings, this invention provides microbe-resistant medical devices and methods of making these medical devices.

In a first aspect, the present invention provides a microbe-resistant medical device. A base coat is applied to at least a portion of a surface of the device. The base coat can be any polymeric material that is capable of being coated onto a medical device.

That base coat includes one or more types of antimicrobial particles that are held in the base coat. The particles may be insoluble antimicrobial particles that are capable of releasing an agent capable of inducing microbial stasis or exhibiting microbicidal effect when the coating comes in contact with aqueous fluid. "Insoluble" refers to the inability of these antimicrobial particles to be dissolved in the solvent systems used with the invention.

A polymeric over coat is applied over at least a portion of the base coat. The over coat may be an organic soluble polymer, a water soluble polymer, a hydrogel or any other polymer capable of being coated onto a medical device. The polymer of the over coat is dissolvable in a solvent that does not dissolve the polymeric base coat during the over coating process. Consequently, the over coat remains substantially free of the antimicrobial particles. This provides increased patient comfort by avoiding the problems discussed above associated with agglomeration of the antimicrobial particles and with bumpy or micro-rough coating surfaces.

In a second aspect, the present invention provides a microbe-resistant polymeric coating. This coating has a polymeric base coat with one or more types of antimicrobial particles. A polymeric over coat is applied over at least a portion of the base coat and remains substantially free of the antimicrobial particles by not dissolving the base coat during the over coating process.

In a third aspect, the present invention provides a method of preparing a microbe-resistant medical device. According to this method, a medical device is provided. A first polymer is dissolved in a first polymer solution. One or more types of antimicrobial particles are dispersed in the first polymer solution to form a first coating solution. The first coating solution is applied to at least a portion of the medical device to form a base coat. This application may be by either spray or dip coating. Then, a second polymer is dissolved in a second solvent system to form a second coating solution. This second solvent system does not dissolve the base coat within the normal exposure time during application of the over coat to the medical device. The second coating is applied to cover at least a portion of the base coat to form an over coat that remains substantially free of the antimicrobial particles. Again, this application may be by either spray or dip coating.

In a fourth aspect, the present invention provides a method of over coating a microbe-resistant medical device. According to this method, a microbe resistant medical device (i.e., a device at least partially surrounded by a polymeric base coat having one or more types of antimicrobial particles disposed in the base coat) is provided. Then, an over coat polymer is dissolved in a solvent system that does not dissolve the base coat during application of the over coat to the medical device. The over coat polymer is applied to cover at least a portion of the microbe-resistant medical device. The over coat is substantially free of the antimicrobial particles. The base coat is not dissolved during application of the over coat.

Medical devices formed as described above exhibit reduced micro-roughness because the antimicrobial particles are not exposed where the over coat covers them. In addition, the over coat can provide lubricity and patient comfort, as well as control of the release of the antimicrobial agents.

DETAILED DESCRIPTION OF THE INVENTION

The microbe-resistant medical devices of the present invention include a base coat having one or more types of antimicrobial particles and an over coat provided over at least a portion of the base coat.

Medical devices are any article that contacts patients or are used in health care, and may be for use either internally or externally. The medical devices can be made from a variety of natural or synthetic materials, such as, for example, latex, polystyrene, polyester, polyvinylchloride, polyurethane, ABS polymers, polyamide, polyimide, polycarbonate, polyacrylates, polyethylene, polypropylene, synthetic rubber, stainless steel, ceramics such as aluminum oxide and glass, and silicone.

Illustrative, non-limiting, examples include cannulae, catheters, condoms, contact lenses, endotracheal and gastroenteric feeding tubes as well as other tubes, grafts, guide wires, implant devices, IUDs, medical gloves, oxygenator and kidney membranes, pacemaker leads, peristaltic pump chambers, shunts, stents and sutures.

The antimicrobial particles can be any substance that releases an agent that is capable of inducing microbial stasis or exhibiting microbicidal effect when present in an effective amount. Methods of determining microbial stasis or microbicidal effect are known in the art and include, for example, measuring the minimum inhibitory concentration of coated catheter extracts, zone of inhibition testing, and bacterial adherence testing, using known clinical pathogens for all tests.

The antimicrobial particles can be metals and metal salts, oxides and complexes having oligodynamic properties, such as aluminum, antimony, bismuth, cerium, copper, gold, iridium, magnesium, mercury, palladium, platinum, silver, tin and zinc and their salts, oxides, complexes and mixtures thereof. The antimicrobial particles may be the same substance (e.g., silver zeolite) or may be different (e.g., a mixture of silver zeolite and silver iodide). The particles may have average particle sizes of up to about 100 microns. Preferably, the antimicrobial particles have average particle sizes of less than about 10 microns and most preferably less than about 4 microns.

For example, the antimicrobial particles include, but are not limited to: copper and its salts, such as copper acetate, copper chloride, copper bromide, copper chlorate, copper perchlorate, copper nitrite and copper nitrate, copper sulfate, and other copper salts and complexes, and silver and its salts, such as silver acetate, silver benzoate, silver chloride, silver carbonate, silver iodate, silver iodide, silver lactate, silver laurate, silver oxide, silver palmitate, silver protein, silver sulfadiazine, silver chloride/titanium dioxide complexes, silver zeolite, and other silver salts and complexes. Other non-copper and non-silver containing antimicrobial particles also may be used.

In some embodiments, the antimicrobial particles may have an average particle size greater than 50 microns. Although it is generally preferred to have antimicrobial particles with average particle sizes less than about 4 microns, in some circumstances it may be advantageous to incorporate such larger antimicrobial particles into the base coat. By using an over coat, enhanced patient comfort is provided while still allowing the use of such larger antimicrobial particles.

The base coat can be any polymer that is capable of being coated on to the surface of the medical device and also is capable of incorporating the antimicrobial particles. Base coat polymers include organic soluble polymers, water soluble polymers and hydrogels. Illustrative examples of polymers for the base coat are polyurethane, polyurea, polyurethaneurea, acrylic copolymers, combinations thereof, and/or block co-polymers derived therefrom. Examples of polyurethane base coats are described in U.S. Pat. Nos. 3,822,238; 3,975,350; 4,156,066; 4,156,067; 4,255,550; 4,359,558; 4,729,914; 4,789,720 and 4,810,543 which are incorporated herein.

The base coat may be applied by dip coating onto the medical device. Polymers that are hard to coat (i.e., polyethylene, polypropylene and polytetrafluoroethylene) may also be used with the present invention. The polymer base coat can be coated as a preformed polymer or it can result from the polymerization of monomers on the surface of the medical device.

The over coat is also a polymer and is applied over at least a portion of the antimicrobial particle containing base coat. The over coat may be any organic soluble polymer, water soluble polymer, hydrogel or any other polymer capable of being coated onto a medical device. Acceptable polymers include the following polymeric materials: polyurethane, polyurethaneurea, polyvinylpyrrolidone, polyethylene oxide, polyacrylic acid, hydroxyethylmethacrylate, carboxymethyl cellulose, polyvinyl alcohol, polyacrylamide, dextran and other polysaccharides, starches, guar, xantham and other gums and thickeners, collagen, gelatins and other biological polymers. Nearly any hydrophilic polymer that can be dissolved in solvents can be used for the over coat.

The hydrogels preferably exhibit about 25% by weight to about 500%, more preferably exhibit about 50% by weight to about 200%, and most preferably exhibit from about 75% by weight to about 150% by weight water uptake. The hydrogels may be derived from water-soluble polymers including, but not limited to, poly(ethylene oxide), poly(ethylene glycol), poly(vinyl alcohol), polyvinylpyrrolidone, poly(ethyloxazoline), polyamino acids, pseudopolyamino acids, as well as mixtures of these with each other or other water-soluble polymers.

These water-soluble hydrogel polymers can be complexed with, covalently bound to or copolymerized with a second polymer, for example, a polyurethane, a polyurea or a polyurethaneurea, as well as mixtures of these with each other or with other polymers. The second polymer can be added as a preformed polymer, or it can result from monomers polymerized in the presence of the water-soluble polymer. The polymerization reaction can take place before or after coating the substrate.

In addition, the over coat polymer—like the base coat polymer—is permeable or semi-permeable to the agent(s) released from the antimicrobial particles. To provide microbial resistance, the antimicrobial particles release their antimicrobial agents into the surrounding fluid or tissue.

Further, the over coat polymer is chosen such that during the coating process the over coating polymer is capable of dissolving in a solvent system that is not capable of dissolving the base coat during the normal course of coating application. For example, the base coat may be a polyurethane resin that is not soluble in alcohol and the over coat can be polyvinylpyrrolidone, an alcohol soluble polymer.

Although the base coat does not dissolve in the over coat solvent system during dipping, it should swell sufficiently to form an interpenetrating network between the base coat and the over coat. This provides coating adherence. However, the base coat should not dissolve or release any significant amounts of the antimicrobial particles into the over coat. Antimicrobial particles, if present in the over coat, should not compromise patient comfort by causing a bumpy or microrough device surface. Eliminating, or at least reducing, leaching of the antimicrobial particles into the over coat solution also eases manufacture as discussed below.

As would be understood by one of skill in the art, solvent systems for use with the base coat or the over coat include any organic or inorganic solvents, water-based solvents or combinations of these that are capable of dissolving these polymers at appropriate processing conditions. Non-limiting examples of solvents include acetone, acetonitrile, aniline, benzene, butanol, carbondisulfide, carbontetrachloride, chloroform, cyclohexane, dimethylacetamide, dimethylsulfoxide, dimethylformamide, dioxane, ethanol, ethyl acetate, ethylene glycol, hexane, isopropyl alcohol, methanol, methylene bromide, methylene chloride, methyl ethyl ketone, nitroethane, pyridine, tetrahydrofuran, tetralin, toluene, trichloroethylene and water.

Medical devices according to the present invention are manufactured by applying a polymeric base coat to the device that includes antimicrobial particles and then applying an over coat on the device with a polymer chosen so that it is dissolvable in a solvent that does not dissolve the base coat during the solution coating process.

The base coat is applied by methods known in the art, including dip coating and spray coating. Typically, these methods involve the dissolution of a polymer in a solvent system, dispersing antimicrobial particles into the resulting polymer solution, and then dipping or spraying of that polymer solution onto the medical device. Then, the base coated medical device is allowed to dry, either at room temperature or at a controlled temperature or both.

Previously, it has been problematic to apply an over coat onto such base coated medical devices. In particular, when dip coating a series of medical devices, if the base coat dissolves even slightly while being coated with the overcoating, the antimicrobial particles could accumulate in the over coat. If this happens, the antimicrobial particles would then begin to collect in the over coat solution, causing the antimicrobial particle concentration to increase in the over coating as a function of the number of devices dipped. Also, antimicrobial particles extracted into the over coat solution could agglomerate into larger particles in the over coat and cause microroughness. As a consequence, the over coating solution must be changed more frequently when the base coat dissolves into the over coat solution. Accordingly, the present invention reduces manufacturing costs and eases manufacture by avoiding these problems.

Moreover, if the polymer base coat dissolves during dip coating (i.e., goes into the over coat solution) the properties of the over coat could adversely be affected. For example, if the base coat is not lubricious when wet, it could reduce the lubricity of a wet-lubricious over coat as its concentration in the over coat increases with the number of base-coated medical devices dipped into the over coat solution.

To address these problems, the over coating is applied by solution coating over the base coat, and the polymer for the over coat is selected so that it is capable of dissolving in a solvent that does not dissolve the base coat during the solution coating process. As with the base coat, once the medical device is coated with the over coat, it is allowed to dry. Again, the over coat may be applied by dip coating or spray coating, as described above. The base coat does not dissolve during the coating process because of exposure to the over coat solvent.

For example, a polyurethane that will not dissolve in a solvent system containing more than 50% denatured ethanol is used for the base coat. An over coat is formed by a very hydrophilic polyurethane that is capable of dissolving in a solvent system containing 85% denatured ethanol. In this embodiment, the over coat is dissolved in a solvent system containing enough of the nonsolvent, ethanol, for the base coat that it does not dissolve the base coat when over coating is performed.

When hydrophilic polymers are used for the over coat, the overcoated antimicrobial medical devices provide increased surface lubricity and decreased surface area (as compared to the base coat) of the medical device. Consequently, increased patient comfort, decreased tissue irritation, and increased antimicrobial effectiveness are achieved. In addition, the over coat permits the use of stronger, less hydrophilic base coat materials than previously permitted where a lubricious device surface is desired. Further, the rate of release of an antimicrobial agent can be modified or controlled by selection of the polymers for both the base and over coats.

Using an over coat with the antimicrobial particle containing base coat reduces concerns about the surface roughness of the base coat. Consequently, high concentrations of the antimicrobial particles are present in the base coat in some embodiments. Any concentration of the antimicrobial particles may be used in the base coat as long as there is sufficient polymer in the base coat to hold the particles in place. For example, the base coat can be provided with antimicrobial particles at concentrations of up to about 75 weight %, more preferably of up to about 50 weight %, and most preferably between about 30 and about 50 weight %.

In some embodiments, more than one over coat and one base coat may be provided on the medical device. For example, a medical device can be provided with two over coat layers. In one such embodiment, a catheter may be provided with a first polymeric over coat designed to control the rate of release of the antimicrobial agent from the base coat, and then may be provided with a second polymeric over coat designed to maximize patient comfort. In addition, the first polymeric over coat may be designed to compatibilize the base coat with the second polymeric over coat. This may be advantageous when the base coat and the second polymeric over coat cannot be sufficiently adhered to one another without an intermediate first polymer over coat.

In other embodiments, a medical device may be provided with two base coats. This may permit, for example, the use of two different antimicrobial particles in the two base coats, when these antimicrobial particles cannot be used in a single base coat. A first one of the base layers may have one type of metallic antimicrobial particle, and a second one of the base layers may have a different type of metallic antimicrobial particle. When these two types of metallic antimicrobial particles are placed in an electrically conducting fluid (e.g., within various bodily fluids), a galvanic cell is created. One metallic antimicrobial particle acts as an anode. The second metallic antimicrobial particle acts as a cathode to drive the electrochemical cell. For example, if copper-based particles are used in one base layer and silver-based particles are used in another, the copper-based particles will act as the anode, releasing $Cu^+$ ions into the electrolyte. The more noble of the metals, silver, acts as the cathode, which does not ionize. Advantageously, such an arrangement forces $Cu^+$ ions into the surrounding environment at a greater rate than if only one type of metallic antimicrobial particles was used. Accordingly, this is another way to alter or control the release rate of antimicrobial agent from the medical device.

Various therapeutic agents may be incorporated into the above-described medical devices. A catheter can be provided with one or more additional therapeutic agents. For example, liquid or solid, soluble antimicrobial agents, antibiotics or anticoagulants, alone or in combination, may be incorporated within the over coat or the base coat. In addition, fillers, extenders, melt flow additives, dry flow additives, pigments and other additives may also be used to enhance specific physical properties, aesthetics, durability or other attributes of the medical devices.

The following example is presented to illustrate the present invention, but is in no way to be construed as limiting the scope of the invention. It will be recognized by those skilled in the art that numerous changes and substitutions may be made without departing from the spirit of the invention. Accordingly, it will be understood that the invention is not to be limited to the embodiments disclosed herein, but is to be understood from the following claims, which are to be interpreted as broadly as allowed under the law.

EXAMPLE 1

A base coat is prepared as follows. A solvent system is formed by mixing 56.25% tetrahydrofuran (THF), 25% methylene bromide and 18.75% denatured ethanol. A polyurethane resin (commercially available from CardioTech International of Woburn, Mass. under the tradename HMBU) is dissolved into the solvent system at a concentration of 3.6% of the total solution weight.

Silver zeolite particles (commercially available from Applied Surface Technology, Inc. of Louisville, Ky. under the tradename AGION®) are dispersed for a total of 44 minutes into the base coat solution at a concentration of 40% of the dry coating weight (combined weights of HMBU and AGION®).

The base coat solution is maintained at a temperature of about 23° C. and applied to a 16 Fr Foley urinary catheter (commercially available from C.R. Bard, Inc. under the tradename BARDEX) by dipping into the coating solution at a controlled speed of 40 inches per minute (ipm), allowed to dwell in solution for 10 seconds and withdrawn from the solution at a speed of 17 ipm.

A second polyurethane (commercially available from CardioTech under the tradename HydroMed D6/40™) is dissolved in a solvent system of 15% THF and 85% denatured ethanol at a temperature of about 40° C., cooled, and maintained at a temperature of about 25° C. to keep the HydroMed D6/40™ in solution. The base coated catheter is then overcoated by dip coating at a speed of 40 ipm into the solution, with no dwell in solution, and is withdrawn at a speed of 17 ipm to apply the over coat.

The over coat solution produces swelling of the base coat sufficient for coating adhesion, but does not dissolve or attack the base coat. The overcoated catheter has reduced microroughness compared to non-overcoated catheters, and has a smooth and wet-lubricious coating on both the inner and outer surfaces of the catheter.

Upon contact with aqueous fluids, catheters coated as described above absorb moisture and become lubricious, or slippery, to the touch. The degree of lubricity of the coating may be measured by a test of Coefficient of Friction (COF).

The catheter prepared as described in Example 1 was tested for COF. A pair of catheters were positioned about 2 inches apart parallel to each other in a trough of water and a 400 g stainless steel sled wrapped with a cellulose membrane was pulled down the shaft of the catheter parallel to the length of the catheter from the funnel end towards the tip. The force required to pull the sled was averaged over a length of the catheter, and this force was divided by the weight of the sled to give a unitless value of COF.

To evaluate lubricity and durability of the coating, catheter is incubated in deionized water at about 37° C. during testing. The COF was measured after one hour, and after 1, 7, 14 and 21 days.

After one hour of incubation, the catheter of Example 1 exhibited a COF of 0.06. Preferably the one hour COF is between about 0.02 and about 0.15, and most preferably between about 0.02 and about 0.08.

The change in COF over the 21 day period was measured to evaluate durability of the catheter of Example 1. In general, durability is demonstrated where the COF increases very little during the 21 days of testing. The catheter of Example 1 exhibited a COF of 0.08 on day 21, as compared with a one hour reading of 0.06. This was considered to be durable.

I claim:

1. A microbe-resistant medical device comprising:
   a substrate;
   a polymeric base coat applied to at least a portion of the substrate;
   at least one type of antimicrobial particle dispersed throughout the base coat; and
   a solid polymeric over coat positioned over at least a portion of the base coat;
   wherein the polymeric over coat is dissolvable in a solvent that does not dissolve the polymeric base coat during application of the over coat, and wherein the polymeric over coat is substantially free of the antimicrobial.

2. The microbe-resistant medical device of claim 1, wherein the substrate comprises at least one material chosen from: latex; polystyrene; polyester;
   polyvinylchloride; polyurethane; ABS polymers; polyamide; polyimide; polycarbonate;
   polyacrylate; polyethylene; polypropylene; synthetic rubber; stainless steel; ceramics; aluminum oxide; glass or silicone.

3. The microbe-resistant medical device of claim 1, wherein the polymeric base coat is chosen from: polyurethane; polyurea; polyurethaneurea; acrylic copolymers; combinations thereof; or block co-polymers derived therefrom.

4. The microbe-resistant medical device of claim 1, wherein the antimicrobial particles comprise silver-based compounds chosen from: silver acetate; silver benzoate; silver chloride; silver carbonate; silver iodate; silver iodide; silver lactate; silver laurate; silver oxide; silver palmitate; silver protein; silver sulfadiazine; silver chloride/titanium dioxide complex; silver zeolite; or other silver salts and complexes.

5. The microbe-resistant medical device of claim 1, wherein the antimicrobial particles have an average particle size of up to about 100 microns.

6. The microbe-resistant medical device of claim 1, wherein the polymeric over coat comprises at least one material chosen from: polyurethane; polyurethaneurea; polyvinylpyrrolidone; polyethylene oxide; polyacrylic acid; hydroxyethylmethacrylate; carboxymethyl cellulose; polyvinyl alcohol; polyacrylamide; dextran; polysaccharides; starches; guar, xanthan and other gums and thickeners; collagen or gelatins.

7. The microbe-resistant medical device of claim 1, wherein the polymeric base coat is a polyurethane resin that is not soluble in alcohol and the polymeric over coat is an alcohol soluble polyvinylpyrrolidone.

8. The medical device of claim 1, comprising more than one base coat.

9. The medical device of claim 1, wherein the coating comprises at least a second polymeric over coat in addition to the solid polymeric over coat.

10. The medical device of claim 1, wherein the over coat comprises a hydrogel.

11. A microbe-resistant polymeric coating for a medical device, the coating comprising:
    a polymeric base coat having antimicrobial particles dispersed throughout; and
    a solid polymeric over coat that is substantially free of the antimicrobial and is positioned over at least a portion of the base coat.

12. The microbe-resistant polymeric coating of claim 11, wherein the polymeric base coat is a polyurethane resin that will not dissolve in a solvent system containing more than 50% denatured ethanol.

13. The microbe-resistant polymeric coating of claim 12, wherein the antimicrobial particles are silver zeolite.

14. The microbe-resistant polymeric coating of claim 13, wherein the silver zeolite is present in the base coat at a concentration of about 40% of the combined dry weight of the polymeric base coat and the antimicrobial particles.

15. The microbe-resistant polymeric coating of claim 14, wherein the over coat is a polyurethane that is capable of dissolving in a solvent system containing 85% denatured ethanol.

16. The coating of claim 11, wherein the coating comprises more than one base coat.

17. The coating of claim 11, wherein the coating comprises at least a second polymeric over coat in addition to the solid polymeric over coat.

18. The coating of claim 11, wherein the over coat comprises a hydrogel.

19. A method of preparing a microbe-resistant medical device comprising:
    providing a medical device having a surface;
    dissolving a first polymer in a first solvent system to prepare a first polymer composition;
    dispersing at least one type of antimicrobial particle in the first polymer composition to form a base coat composition;
    applying the base coat composition to at least a portion of the surface to form a base coat;
    dissolving a second polymer in a second solvent system to form a second polymer composition; and
    applying the second polymer composition on to at least a portion of the base coat such that the base coat is not dissolved during application of the second polymer composition and forms a solid over coat substantially free of the antimicrobial.

20. The method of preparing a microbe-resistant medical device of claim 19, wherein the medical device is chosen from: cannulae; catheters; condoms; contact lenses; endotracheal and gastroenteric feeding tubes as well as other tubes; grafts; guide wires; implant devices; IUDs; medical gloves; oxygenator and kidney membranes; pacemaker leads; peristaltic pump chambers; shunts; stents or sutures.

21. The method of preparing a microbe-resistant medical device of claim 20, wherein the medical device is a urinary catheter.

22. The method of preparing a microbe-resistant medical device of claim 19, wherein the base coat is applied by dip coating.

23. The method of preparing a microbe-resistant medical device of claim 19, wherein the base coat is applied by spray coating.

24. A medical device prepared by the method of claim 19.

25. A medical device prepared by the method of claim 20.

26. A medical device prepared by the method of claim 21.

27. The method of claim 19, further comprising applying a second base coat composition.

28. The method of claim 19, further comprising applying a second over coat composition.

29. A method of overcoating a microbe-resistant medical device, the method comprising:
    providing a microbe-resistant medical device at least partially surrounded by a polymeric base coat having at least one type of antimicrobial particle dispersed throughout the base coat;
    dissolving an over coat polymer in a solvent system that does not dissolve the base coat during application of the over coat polymer; and
    applying the dissolved over coat polymer to at least a portion of the microbe-resistant medical device to form a solid over coat such that the base coat is not dissolved and the over coat is substantially free of the antimicrobial.

30. The method of claim 29, further comprising applying a second over coat composition.

31. The method of claim 19, wherein the over coat comprises a hydrogel.

32. The method of claim 29, further comprising applying a second base coat composition.

33. The method of overcoating a microbe-resistant medical device of claim 29, wherein the solvent system that does not dissolve the base coat comprises at least one solvent chosen from: acetone; acetonitrile; aniline; benzene; butanol; carbondisulfide; carbontetrachloride; chloroform; cyclohexane; dimethylacetamide; dimethylsulfoxide; dimethylformamide; dioxane; ethanol; ethyl acetate; ethylene glycol; hexane; isopropyl alcohol; methanol; methylene bromide; methylene chloride; methyl ethyl ketone; nitroethane; pyridine; tetrahydrofuran; tetralin; toluene; trichloroethylene; or water.

34. The method of overcoating a microbe-resistant medical device of claim 32, wherein the over coat is applied by dip coating over the base coat.

35. The method of overcoating a microbe-resistant medical device of claim 32, wherein the over coat is applied by spray coating over the base coat.

36. A medical device prepared by the method of claim 32.

37. A urinary catheter prepared by the method of claim 29.

38. The method of claim 29, wherein the over coat comprises a hydrogel.

* * * * *